United States Patent
Ro et al.

(10) Patent No.: US 6,193,759 B1
(45) Date of Patent: Feb. 27, 2001

(54) MODULAR LONG STEM HIP TRIAL

(75) Inventors: Gloria Ro, Quincy; Kimberly A. Dwyer, Marion; Corey Wilson-Wirth, Milton, all of MA (US)

(73) Assignee: Depuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/008,866

(22) Filed: Jan. 20, 1998

Related U.S. Application Data

(63) Continuation-in-part of application No. 08/884,588, filed on Jun. 27, 1997, now Pat. No. 5,888,208, which is a continuation-in-part of application No. 08/824,336, filed on Mar. 26, 1997, now Pat. No. 5,860,982.

(51) Int. Cl.$^7$ ..................................... A61F 2/32
(52) U.S. Cl. .................. 623/23.28; 623/23.18; 623/23.25
(58) Field of Search ................. 606/86, 87, 89, 606/90, 92, 99, 100, 102, 53, 63, 79; 623/16, 18, 19, 22, 23, 23.18, 23.25, 23.28

(56) References Cited

U.S. PATENT DOCUMENTS

| | | | |
|---|---|---|---|
| 4,135,517 | 1/1979 | Reale | 128/303 |
| 4,163,292 * | 8/1979 | Averett, Jr. | 623/23 |
| 4,601,289 | 7/1986 | Chiarizzio et al. | 128/305 |
| 4,658,808 | 4/1987 | Link | 623/16 |
| 4,908,032 * | 3/1990 | Keller | 623/23 |
| 4,919,678 * | 4/1990 | Kranz | 623/23 |
| 4,938,773 * | 7/1990 | Strand | 623/22 |
| 4,963,155 | 10/1990 | Lazzeri et al. | 623/23 |
| 5,032,130 | 7/1991 | Schekhas et al. | 623/23 |
| 5,074,879 | 12/1991 | Pappas et al. | 623/18 |
| 5,080,685 | 1/1992 | Bolesky et al. | 623/23 |
| 5,100,407 | 3/1992 | Conrad et al. | 606/79 |
| 5,108,437 | 4/1992 | Kenna | 623/16 |
| 5,108,452 | 4/1992 | Fallin | 623/23 |
| 5,342,366 * | 8/1994 | Whiteside et al. | 606/102 |
| 5,507,817 | 4/1996 | Craig et al. | 623/18 |
| 5,507,830 | 4/1996 | DeMane et al. | 623/23 |
| 5,569,263 | 10/1996 | Hein | 606/102 |
| 5,601,567 | 2/1997 | Swajger et al. | 606/102 |
| 5,653,765 * | 8/1997 | McTighe et al. | 623/23 |
| 5,702,480 * | 12/1997 | Kropf et al. | 623/23 |
| 5,766,261 * | 6/1998 | Neal et al. | 623/16 |
| 5,876,459 * | 3/1999 | Powell | 623/23 |

FOREIGN PATENT DOCUMENTS

| | | | | |
|---|---|---|---|---|
| 0887053 | 12/1998 | (EP) | | A61F/2/46 |
| 9407438 | 4/1994 | (WO) | | A61F/2/34 |

OTHER PUBLICATIONS

Brochure entitled PERFECTA PDA Calcar, dated Oct. 1995.

Howmedica hnr brochure, including article entitled Head/Neck Replacement Surgery in Hip Fractures of the Elderly by Ronald Joseph, M.D., Ph.D. , Orthopaedic Surgeon, Good Samaritan Hospital, San Jose, California, pp. 2–15, ©7/93.

Howmedica hnr brochure, Head/Neck Replacement, 4 pages dated Jul. 1993.

Zimmer modular Calcar brochure, 5 pages showing tools and Steps 1–16, ©1992

Wright Medical Technology, Inc. brochure entitled *PERFECTA/PDA*, 4 pages, ©1996.

Brochure entitled *Cemented Hip Systems Surgical Technique*, Johnson & Johnson Orthopaedics, pp. 1–8, dated May 1996.

* cited by examiner

*Primary Examiner*—Michael J. Milano
(74) *Attorney, Agent, or Firm*—Nutter, McClennen & Fish, LLP

(57) ABSTRACT

A prosthetic trial for a femur includes a curved stem rotatably engaged with a body that defines a trunnion. A locking mechanism inhibits rotation of the body with respect to the stem. The trial is configured for either left or right femoral implantation by rotating the stem with respect to the body to orient the stem in the appropriate direction.

9 Claims, 7 Drawing Sheets

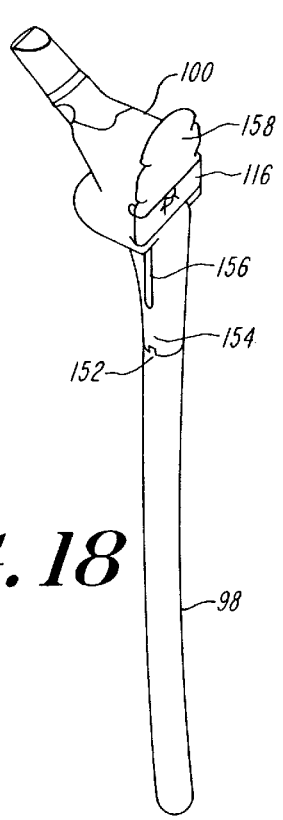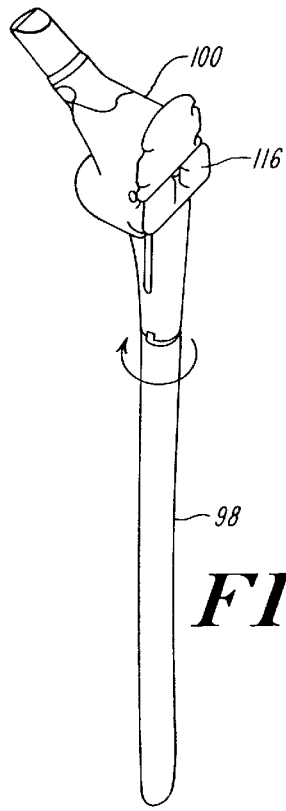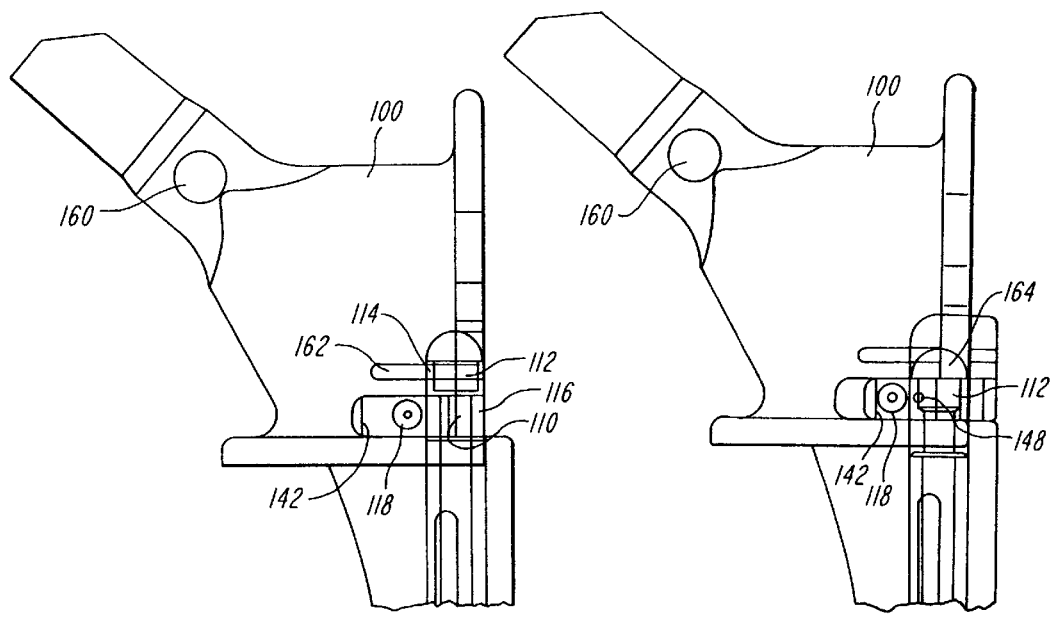
FIG. 18  FIG. 20  FIG. 19  FIG. 21

MODULAR LONG STEM HIP TRIAL

CROSS REFERENCE TO RELATED APPLICATIONS

This application is a continuation-in-part of U.S. Ser. No. 08/884,588, filed Jun. 27, 1997 and issued Mar. 30, 1999 as U.S. Pat. No. 5,888,208, which is a continuation-in-part of U.S. Ser. No. 08/824,336, filed Mar. 26, 1997, and issued Jan. 19, 1999 as U.S. Pat. No. 5,860,982.

STATEMENT REGARDING FEDERALLY-SPONSORED RESEARCH

Not Applicable.

FIELD OF THE INVENTION

The present invention relates to a device used in arthroplasty, such as a trial for determining the required dimensions of a prosthetic femoral component.

BACKGROUND OF THE INVENTION

A successful hip replacement or arthroplasty procedure results, in part, from selection of prosthetic joint components that are dimensioned and positioned to closely approximate or replicate the geometry and functional characteristics of a natural, healthy hip joint. Typically, the component selection process includes a pre-operative analysis of joint images. However, it has been discovered that a valuable adjunct to image analysis is the temporary fixation of one or more provisional components to a bone or bones of interest at a stage of the arthroplasty procedure prior to permanent fixation of the prosthetic joint. The provisional components are intended to mimic certain aspects of the permanent prosthetic joint in order for a surgeon to validate measurements and to test or "try-out" several different possible component sizes and configurations. Hence, provisional components are aptly known as "trials."

In a known procedure, a trial for a femoral component is used in the following manner. The proximal end of a femur is resected and the medullary canal of the femur is reamed. A broach is inserted into the resected proximal end of the femur to provide a cavity within the bone dimensioned and contoured to receive a femoral stem. However, prior to removing the broach, a trial neck or trunnion and trial head can be secured to the broach to simulate a complete femoral stem. Normally, several neck and head trials of varying lengths and geometries are successively joined to the broach in an attempt to determine an appropriate neck length and overall femoral stem length. Once these lengths have been determined, the trial neck and head are removed from the broach and the broach is removed from the femur. Subsequently, a femoral stem of the appropriate length is selected for insertion into the cavity defined by the broach using techniques known to those skilled in the art.

Other techniques require that the broach be removed from the medullary canal to allow a trial having a stem portion to be used, in addition to a trial head and neck. For example, U.S. Pat. No. 5,100,407 discloses a system including a group of variously sized trial neck/body portions and a group of differing length trial stem portions which are mixed and matched to create a suitable trial. However, repetitive removal and insertion of successions of trial stems accompanied by successive assembly and disassembly with respect to the body can consume a lengthy and costly period of time. Another known trial includes a stem to which a collar is secured at successive points along the length of the trial until an appropriate neck length and stem length have been ascertained. Undesirably, this type of trial induces measurement inaccuracies resulting from stem movement as the collar is repeatedly engaged with and disengaged from the stem. Additionally, as the collar is moved toward the distal end of the stem, less and less of the stem is disposed within the medullary canal, causing the trial to become increasingly unstable and rendering accurate measurements very difficult to achieve.

Other anatomical considerations can further, and undesirably, increase the number of trial components in a kit. For example, trials for long hip stems must be different for the right and left femur due to the curvature or bow of the respective femurs. In other words, a long left stem trial cannot be used in the right femur and vice versa. It is believed that a trial system consisting of numerous parts that must be selected and mated in various combinations, possibly many times, is cumbersome, unnecessarily complex which wastes surgical time, among other deficiencies.

SUMMARY OF THE INVENTION

The present invention overcomes the disadvantages of known trials by providing a unified assembly that facilitates very accurate measurements in a convenient, easy to use manner. The trial does not require repeated assembly and disassembly, and it is uniquely able to provide a geometry that closely approximates a broached cavity, regardless of the height of the trial.

In an exemplary embodiment, a prosthetic trial includes a stem having a proximal end and a distal end, and a body. The body is engaged with the stem near the proximal end of the stem and is slidable with respect to the stem. A locking mechanism can be provided for inhibiting movement of the body with respect to the stem. A collar can extend radially outward from the stem to surround a portion of the body. The body and stem can be configured so that the diameter of the prosthetic trial at a point between the collar and the distal end of the stem increases as the body is moved toward the distal end of the stem and decreases as the body is moved away from the distal end of the stem. Additionally, the proximal end of the stem can include engagement structures such as opposed notches that are engagable by a forked tool.

In another embodiment of the invention, a prosthetic trial includes a proximal stem portion engagable with a distal stem portion. A single distal stem portion can be curved and reversibly securable to the proximal stem portion to provide a long stem trial suitable for procedures for either the right or the left femur. The trial can include a slidable body portion to allow the height of the trial to be adjusted.

In yet another embodiment of the invention, a prosthetic trial includes a stem having a proximal end and a distal end, and a body defining a trunnion. The body is rotatably engaged with the stem to provide a single trial suitable for use in both a left and a right long bone, such as the femur.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein:

FIG. 18 is a perspective view of an assembled trial in a locked state;

FIG. 19 is a detailed view of the locking mechanism in a locked state;

FIG. 20 is a perspective view of an assembled trial in an unlocked state; and

FIG. 21 is a detailed view of the locking mechanism in an unlocked state.

DETAILED DESCRIPTION OF THE INVENTION

Figure 1:
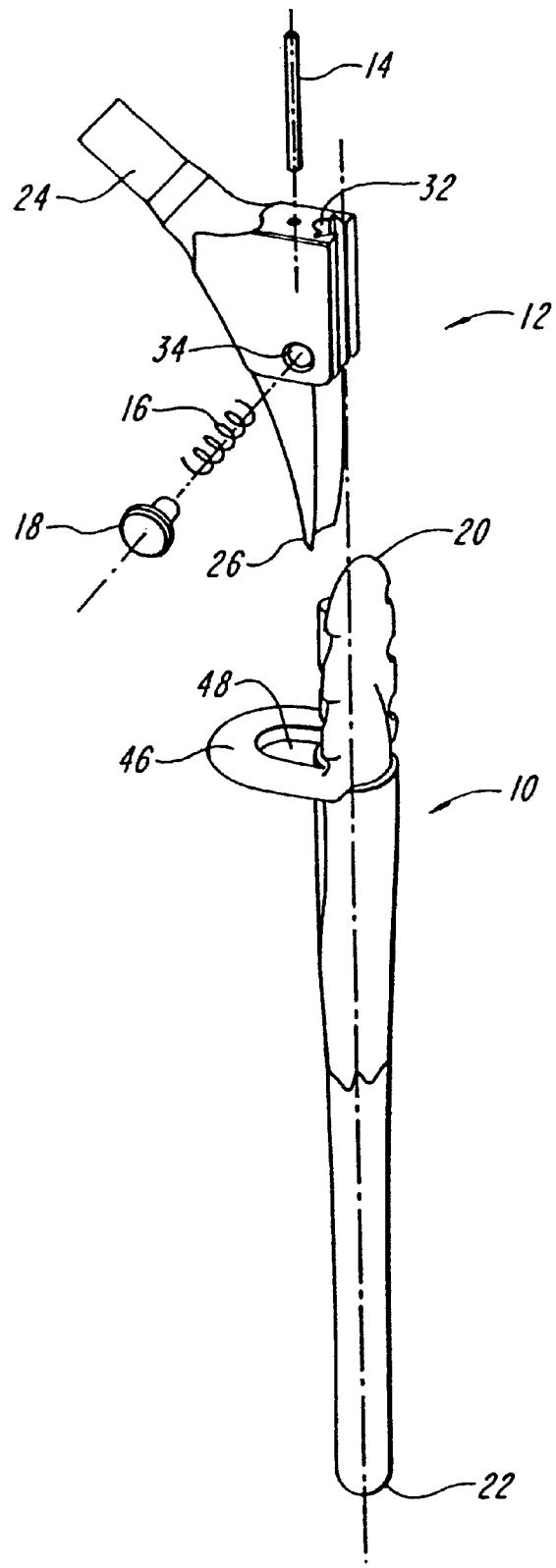
FIG. 1 is an exploded view of the trial in accordance with the invention that illustrates a body portion and a stem portion.

Referring to FIG. 1, a trial in accordance with the invention is shown in an exploded view to show a stem 10, a body 12, a pin 14, a spring 16, and a push-button 18. The stem 10 has a proximal end 20 and a distal end 22, and the body 12 has a proximal end defining a trunnion 24 and a distal end 26. The body 12 is engagable with the stem 10 near the proximal end of the stem so as to be slidable with respect to the stem a predetermined distance between the proximal end and the distal end of the stem.

Figure 2:
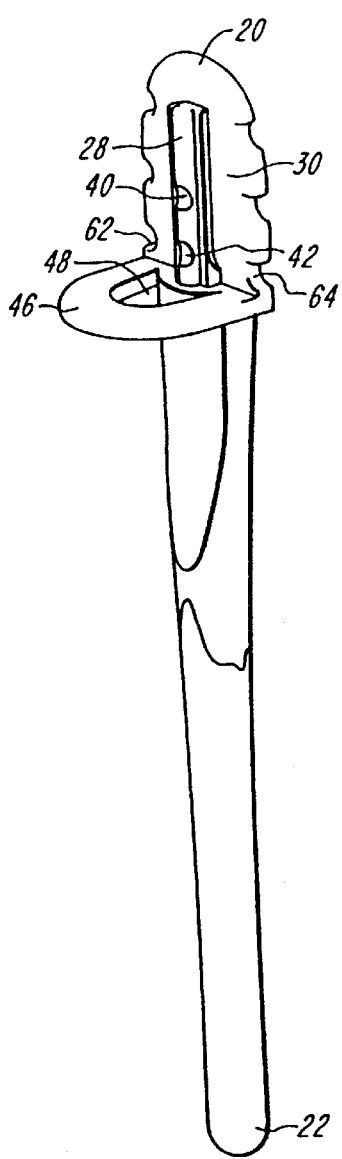
FIG. 2 is a perspective view of the stem portion of the trial shown in FIG. 1.

A guide or track can be associated with either or both of the body 12 and the stem 10 to guide movement of body with respect to the stem. For example, as shown in FIG. 2, the stem 10 includes a track 28 protruding from a first face 30 of the stem and extending a predetermined distance between the proximal end 20 and the distal end 22 of the stem. As shown in FIG. 1, the body 10 includes a notch 32 for receiving the track 28. However, in other embodiments, the body 12 includes a raised portion that is engagable with a track that is recessed within the stem. Regardless of its configuration, the complimentary guide/track/notch of the body and stem serve to limit movement of the body 12 along a predetermined path, such as longitudinal movement, as well as to inhibit undesired movements such as twisting or lateral displacement.

Figure 4:
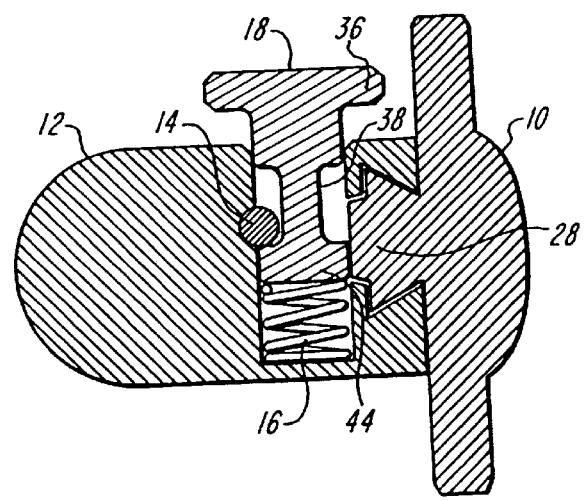
FIG. 4 is a sectional view of a trial showing a locking mechanism in an engaged position.
Figure 5:
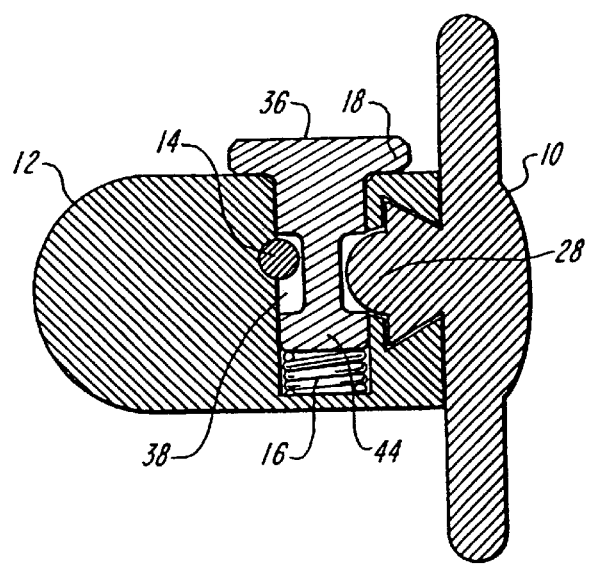
FIG. 5 is a sectional view of a trial showing the locking mechanism in a disengaged position.
Figure 3:
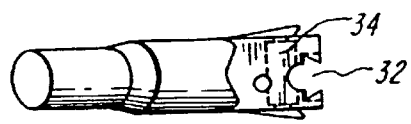
FIG. 3 is a top view of the body portion illustrated in FIG. 1.

Additionally, a locking mechanism can be provided for inhibiting movement of the body 12 with respect to the stem 10. As shown in FIGS. 1 and 3, the body 12 can include a channel 34 that is transverse to the notch 32 and which is adapted to receive an elongate portion of the button 18 therein. The button 18 is movable within the channel from a first position, wherein a portion of the button contacts and engages a portion of the track 28 of the stem, to a second position wherein the button is disengaged from the track. As shown in FIG. 4, the button 18 is biased to the first position by the spring 16. FIG. 5 illustrates the button 18 in the second position. The button 18 includes an expanded head portion 36 that engages the body 12 to limit insertion depth of the button 18 into the body. The button 18 also includes a cut-out portion 38 into which the pin 14 and a portion of the track 28 are received. It will be noted most clearly in FIG. 2 that the track includes first and second transverse grooves 40 and 42. When the body 12 and the stem 10 are caused to slide with respect to each other, the cut-out portion 38 rides over/along the track 28 until a groove 40, 42 is reached, whereupon an end portion 44 of the button is biased into the groove 40, 42. The end portion 44 is released from the groove 40, 42 by pushing the button 18 into the body 12 with enough force to overcome the bias force of the spring 16.

Figure 6:
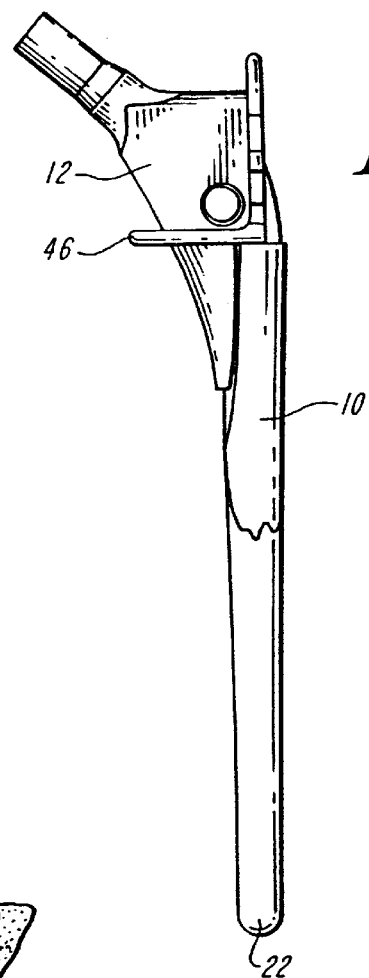
FIG. 6 is a side view of the trial of FIG. 1 in an assembled configuration.
Figure 7:
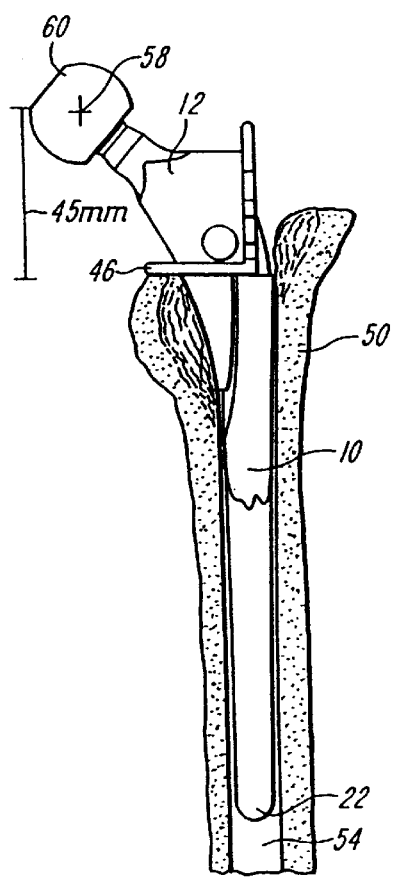
FIG. 7 is a side view of the trial in accordance with the invention inserted into a femur at a first body height.
Figure 8:
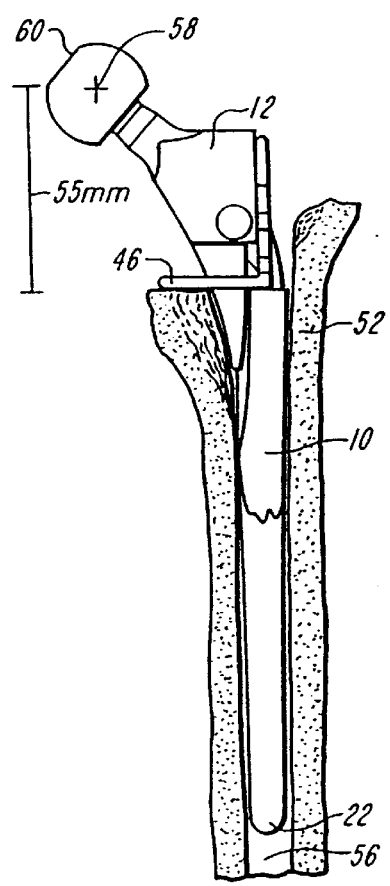
FIG. 8 illustrates a trial in accordance with the invention inserted into a femur at a second body height.
Figure 9:
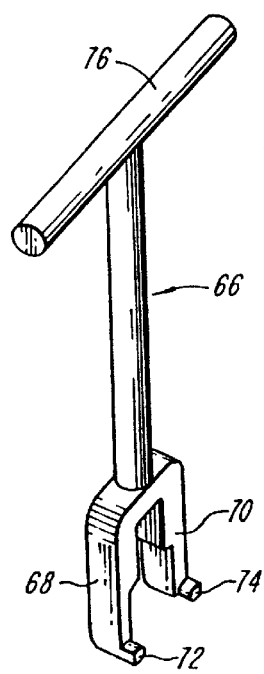
FIG. 9 is a perspective view of an inserter/extractor tool.

Referring again to FIGS. 1 and 2, a collar 46 extends radially outward from the stem. The collar 16 surrounds a portion of the body 12, as shown in FIG. 6, and it is dimensioned to be disposed on a resectioned bone surface as shown in FIGS. 7 and 8. The collar 46 and the distal end of the stem 22 are a fixed distance apart. The collar defines an aperture 48 having curves to compliment the shape of the body 12 and into which the body is received.

Turning now to FIGS. 7 and 8, use of the prosthetic trial is illustrated with respect to resectioned femurs 50 and 52 respectively. Once the femur has been prepared to receive the trial, the distal end 22 of the trial is inserted into the medullary canal 54, 56. It should be noted that in both FIGS. 7 and 8 the full length of the stem 10 from the collar 46 to the distal end of the stem 22 is inserted into the medullary canal. This enables a surgeon to verify that the medullary canal has been reamed to a sufficient depth and width to accommodate a replacement hip stem. The surgeon then slides the body 12 with respect to the stem as required to adjust the head height or distance between a reference point 58 on a head 60 affixed to the body 12 and the collar 46 to determine a prosthetic hip stem length. In FIG. 7, the body 12 is positioned with respect to the stem 10 at a head height of 45 mm, whereas in FIG. 8 the head height is 55 mm. The trial is then removed from the medullary canal and a prosthetic hip stem having the determined length is selected from a group of hip stems. The selected hip stem is cemented into the medullary canal.

It should be noted in these illustrations that the proximal portion of the trial underneath the collar is wider than an intermediate portion of the stem or its distal end 22 to ensure a tight fit of the trial within the femur. The trial is slightly larger than an actual replacement stem in the proximal section below the collar to allow the trial to fill the medullary canal which has been reamed to be slightly larger than an actual replacement stem (to leave room for bone cement to surround the replacement stem). Also, the stem 10 and the body 12 are configured so that a diameter of the trial at a point between the collar and the distal end of the stem increases as the body is moved toward the distal end of the stem and decreases as the body is moved away from the distal end of the stem. Thus, regardless of where a resection cut is made, the dimensions and shape of the trial correspond to the dimensions and shape of the broached medullary canal.

As the trial is usually seated within the medullary canal very snugly, the trial in accordance with the invention further includes features that are of use when inserting the trial into or extracting the trial from the medullary canal. For example, referring to FIG. 2, the proximal end of the stem includes a tool engagement structure, such as a pair of opposed notches 62 and 64 on the stem. A tool 66, shown in FIG. 10, includes a first fork portion or furcation 68 and a second furcation 70 for engaging the opposed notches 62 and 64. The space between the furcations corresponds to the shape of the body 12 to allow the tool to snugly interfit with the body. This ensures that the tool remains axially aligned with the body 12 and the stem 10. Each furcation 68 and 70 can include angled end portions or tines 72 and 74, respectively. A handle 76 provides an easily graspable structure for pulling or pushing tool 66 as well as a suitable surface for mallet striking. Because the notches 62, 64 are similar to the notches of a replacement stem, used to orient cerclage cables, the same tool 66 can be used to insert and extract both the trial and the replacement stem.

Figure 10:
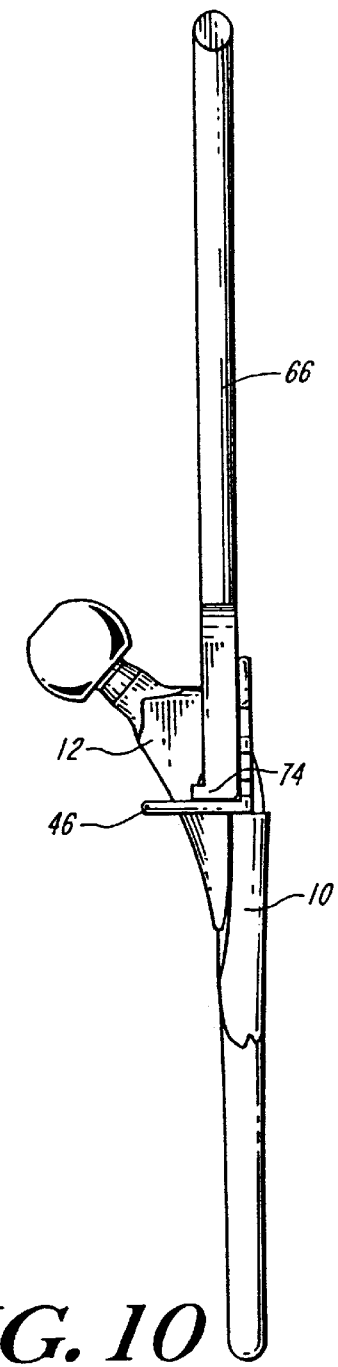
FIG. 10 illustrates the tool of FIG. 9 engaged with a trial for insertion of the trial into a femur.

FIG. 10 shows the tool 66 positioned with respect to the trial for insertion of the trial into a medullary canal, wherein the tines 72, 74 are not engaged with the notches 62, 64, but rest directly upon the collar 46 on opposite sides of the body 12.

Figure 11:
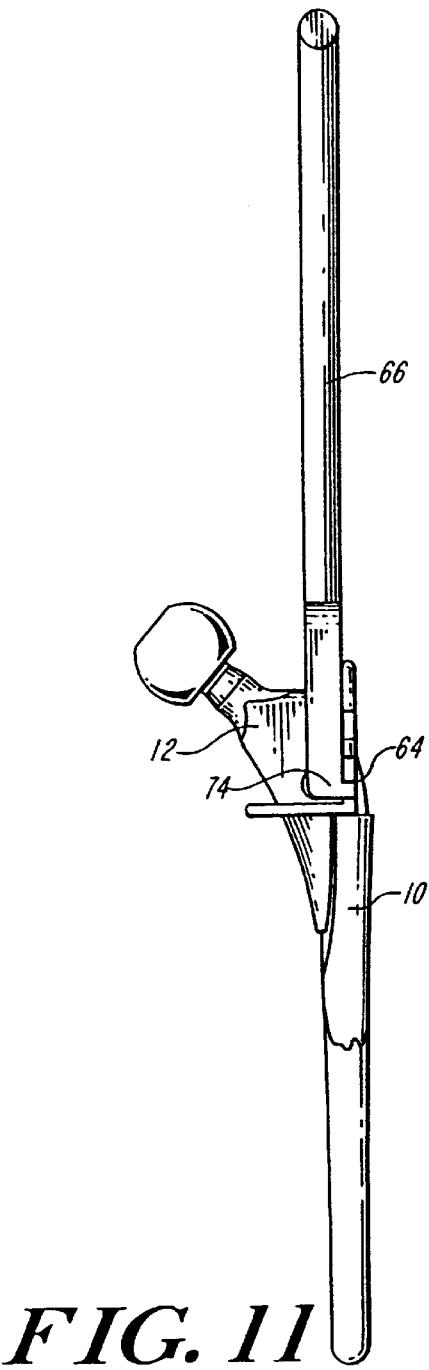
FIG. 11 illustrates the insertion/extraction tool in an extraction position.

FIG. 11 shows the tool 66 positioned with respect to the trial for extraction of the trial from a medullary canal, wherein the tines 72, 74 are engaged with the notches 62, 64. The forked tool thus allows an even and distributed force to be applied to the stem 10 during both insertion and extraction.

Yet another problem with trials, particularly trials for long hip stems, it that a long trial must account for the curvature or bow of the femur. Accordingly, the present invention further provides a modular stem that, depending on the configuration of a distal stem portion, can lengthen the trial stem and provide required curvature for appropriate femoral implantation.

Figure 12:
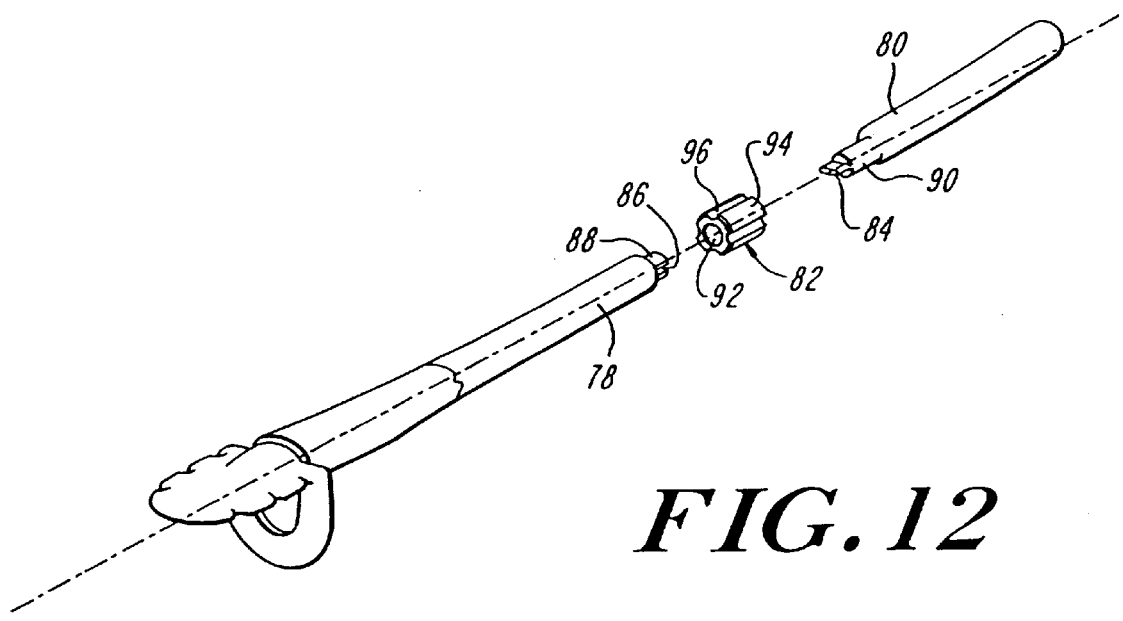
FIG. 12 is an exploded view of an embodiment of a trial having a modular stem portion.

For example, FIG. 12 is an exploded view of an embodiment of a trial having a proximal stem portion 78, a distal stem portion 80, and a connecting element 82. The proximal stem portion 78 can include one or more of the features described above with respect to engagement of a body 12 or with respect to a tool 66. Alternatively, the proximal stem portion 78 can include none of the above inventive features, but rather features found in trials known in the art.

In the illustrated embodiment, the proximal stem portion 78 is about the same length as the stem portion 10 illustrated in FIGS. 1–11 and is therefore usable as described above without the addition of the connecting element 82 or the distal stem portion 80. However, when the distal stem portion 80 is joined to the proximal stem portion 78 the total length of the trial is equivalent to that of a traditional single-piece, long-stem trial. In other embodiments, the proximal stem portion 78 is longer or shorter than the stem portion 10, and the distal stem portion 80 is correspondingly shorter or longer than that illustrated in FIG. 12.

Although the distal stem portion 80 can be straight or coaxial with the proximal stem portion 78, in the illustrated embodiment it is curved or includes an angulation so that some or all of the distal stem portion is not coaxial with the proximal stem portion. The curvature or the angulation can be provided by the shape of the distal stem portion and/or by joining the stem portions together at an angle. Collectively, curvature or angulation of the stem or stems is referred to as "curved."

Continuing to refer to FIG. 12, the distal stem portion 80 is selectively, reversibly attachable to the proximal stem portion 78 to cause the trial to have a curve in a first or a second opposing direction. Thus, the trial can be used for either the right or the left femur without requiring an additional part. In the illustrated embodiment, structures that facilitate reversibility include a tang 84 on the distal stem portion 80 that is receivable within a slot 86 defined by the proximal stem portion 78. The tang 84 and the slot 86 ensure that the distal and proximal stem portions are mated at a precise orientation, and that the orientation cannot be inadvertently changed. For example, were the stem portions to be joined simply by friction fitting a cylindrical element into a cylindrical bore, or by a threaded connection, precise orientation could not be assured.

The slot 86 and tang 84 can be located on reduced diameter portions 88 and 90 of the respective proximal stem portion 78 and the distal stem portion 80. The reduced diameter portions 88 and 90 can be threaded and receivable within a threaded bore 92 of the connecting element 82. The connecting element 82 can include texturing such as alternating elongate ridges 94 and depressions 96 to enable the connecting element to be grasped by hand or with a tool and rotated with respect to the stem portion or portions to create a threaded engagement between the stem portions. Thus, the connecting element locks the stem portions together. However, other embodiments are contemplated that allow the stem portions to be joined in one of two or more precise orientations and be held together without a separate connecting element.

Figure 13:
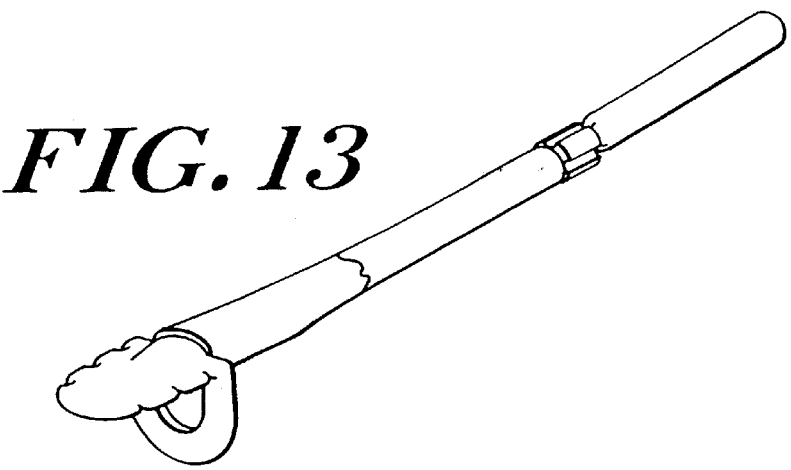
FIG. 13 depicts the trial of FIG. 12 in an assembled state.

FIG. 13 depicts the trial of FIG. 12 in an assembled state. It should be noted that the connecting element 82 has a maximum diameter that approximates that of the stem portions where they join the connecting element.

Figure 14:
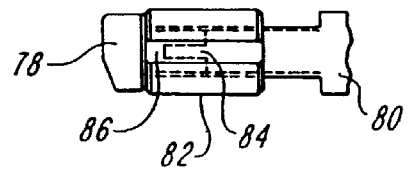
FIG. 14 is a partial cut-away view of a connection between a first stem portion and a second stem portion.

FIG. 14 is a partial cut-away view of a connection between the proximal stem portion 78 and the distal stem portion 80 which clearly shows the engagement of the tang 84 with the slot 86. Although the illustrated tang and slot provide an excellent reversible connection, other structures for joining the stem portions are contemplated and the particular connection is not a limitation of the invention.

Figure 15:
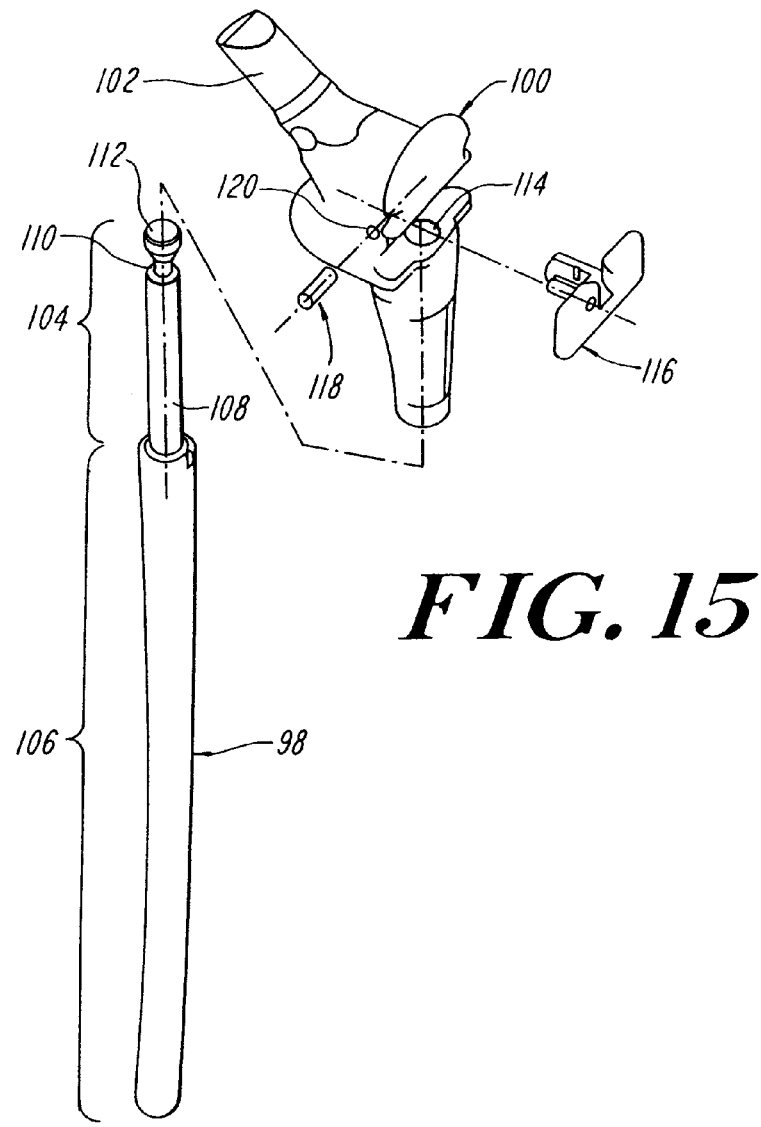
FIG. 15 is an exploded view of another embodiment of a prosthetic trial in accordance with the invention.

FIG. 15 is an exploded view of yet another embodiment of a trial, wherein a stem 98 is rotatable with respect to a body 100 that defines or includes a trunnion 102. The stem 98 includes a proximal end 104 and a distal end 106. The stem 98 is curved for anatomical correctness as required by its length.

Reduced diameter portions 108, 110, 112 of the stem 98 are capable of being inserted into a bore 114 within the body 100. A first locking mechanism 116 is engagable with the body to inhibit withdrawal of the proximal end 104 of the stem 98 from the bore 114 and to provide the proximal end a limited range of travel within the bore. A pin 118, insertable through an aperture 120 in the body 100, is used to limit movement of the first locking mechanism 116 with respect to the body.

Figure 16:
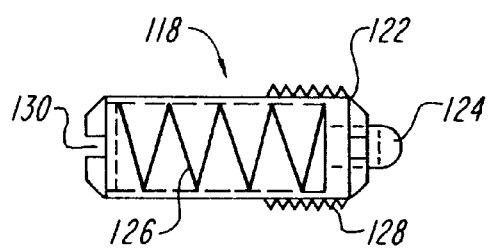
FIG. 16 is a plan view of a pin illustrated in FIG. 15.

FIG. 16 shows the pin 118 in greater detail. The pin 118 is a substantially cylindrical body 122 having a protuberance 124 extending from one end. A bias element 126, such as a spring or elastic body is positioned within the body 122 so that it exerts an outward bias on the protuberance 124. The exterior of the body can include threads 128 that compliment threads (not shown) in the receiving aperture 120 of the body for secure engagement of the pin 118 within the body 110. A slot 130, socket, or other engagement feature for a tool, such as a screwdriver or an Allen wrench, can be provided at one end of the pin to facilitate pin and body mating.

Figure 17:
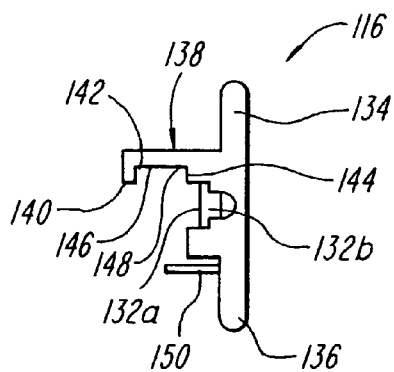
FIG. 17 is a plan view of a portion of a locking mechanism illustrated in FIG. 15.

FIG. 17 is a plan view of the first locking element 116. The locking mechanism 116 includes a region 132a having a first diameter and region 132b having a second diameter, wherein the first diameter is greater than the second diameter. When the first locking element is engaged with the body 100, the region 132 defines a portion of the bore 114 (or an extension thereof) through the body. Moving the first locking mechanism 116 with respect to the body 100, as shown and described with respect to FIGS. 18–21 below, increases or decreases the local diameter of the bore 114.

Finger tabs 134 and 136 are provided to facilitate pushing and pulling the first locking device 116 with respect to the body 100. An arm 138 extends perpendicularly from the plane defined by the finger tabs 134, 136 into or around a portion of the body 100. A nub 140 extends from the arm 138 to provide a first abutment surface 142 on the opposite side of the bore 114 from the finger tabs. A second abutment surface 144 opposes the first abutment surface 142.

When the first locking device 116 and pin 118 are engaged with the body 100, the first and second abutment surfaces 142 and 144, respectively, are on opposite sides of the protuberance 124. The protuberance 124 is biased against a face 146 of the arm 138, and the spacing between the abutment surfaces 140, 144 defines the travel limit of the first locking device. A recess, groove or detent 148 in the face 146 is dimensioned to receive at least a portion of the protuberance 124. When the first locking device 116 is positioned so that the protuberance 124 is received within the detent 148, movement of the first locking device is inhibited until sufficient force is applied to the first locking device (by pulling) to overcome the biasing force applied to the protuberance by the bias element 126. A retaining pin 150, receivable within a bore (not shown) in the body 100, is provided on the first locking device 116 to prevent the first locking device from being displaced from the body in the direction of the biasing force.

Referring now to FIG. 18, a fully assembled trial is illustrated in the locked state and configured for implantation. In this view, a second locking device is shown that includes a tang 152 associated with the stem 98, that is seated within a notch 154 associated with the body 100. A second notch (not shown) is provided in the body 100 directly opposite (180 degrees from) the first notch 154. The second locking mechanism inhibits rotation of the body 100 with respect to the stem when the notch and tang are mated. In other embodiments, the tang is associated with the body and the notches are associated with the stem.

A slot 156 that gives access to the bore 114 in the body 100 can be provided to allow for removal of tissue or foreign matter from the bore, or simply cleaning, without fill disassembly of the trial.

It should be noted that in the locked state, the first locking device 116 is substantially flush with a portion of the body 100 or within the geometric profile of the body. In the illustrated embodiment, the first locking device is flush with a flange element 158. However, the existence of a flange is not important to the invention, nor is the particular shape of the body.

As illustrated in FIG. 19, in the locked state, the reduced diameter portion 110 of the stem is surrounded by region 132b of the locking device 116 which has a smaller diameter than portion 112 of the stem. Thus, portion 112 is trapped or held by the first locking mechanism 116 at its most inserted distance into the bore 114 and the stem 98 cannot be pulled away from the body 100 far enough to dislocate the tang 152 from the notch 154. The protuberance 124 of pin 118 is seated in the detent 148 (see FIG. 17). Thus, the pin 118 acts as a locking mechanism for the first locking mechanism 116.

FIG. 19 also depicts a transverse bore 160 through the trunnion. Not only does the bore 160 readily identify the device as a trial, but it also allows a rod other tool (not shown) to be inserted into or though the bore 160 to facilitate extraction of the trial from a reamed bone canal where it has been temporarily implanted. A slot 162 allows the trial to be cleaned without full disassembly of the trial, or for body tissue or foreign matter to be removed from the bore 114.

Referring now to FIG. 20, a fully assembled trial is illustrated in the unlocked state, wherein the first locking device 116 is pulled out from the body 100. The stem 98 is being rotated in the direction of the arrow to align the second notch (located opposite notch 154) with the tang 152 (see FIG. 18) to configure the long stem trial for a left femur. In the unlocked state, the tang 152 is not seated within the notch and the stem 98 is freely rotatable with respect to the body 100.

As illustrated in FIG. 21, in the unlocked state, the first locking device 116 is pulled away from the body 100 far enough to allow the reduced diameter portion 112 to move into the area of the bore 114 defined in part by region 132a of the locking device 116. As the stem descends (moving away from the body) the second locking device (tang and notch) disengage. However, because the stem 98 is terminated with a head 164 that is wider than the diameter of the bore defined in part by region 132a, the stem does not completely separate from the body. As shown in FIG. 21, protuberance 124 of the pin 118 is disengaged from the detent 148 and the protuberance and pin confront an abutment surface 142.

Many functional advantages are derived from the above-described features. For example, the notch and tang anti-rotational lock only permits two assembled configurations, wherein each position provides appropriate geometry. There is no possible inadvertent or "slightly off" position. Although a notch and tang are disclosed, other geometries and structures are contemplated that achieve a similar function. Also, it should be noted that as the first and second locking devices are completely within the implant geometry when locked, the trial closely replicates the profile of an actual implant. Furthermore, because the trial can be configured so that a reduced diameter portion of the stem portion protrudes into the body portion close to the proximal end of the trial, the stem portion is easily retrieved if the body and stem become separated because the proximal end of the stem is near or protrudes from the opening of the reamed bone canal.

Although the invention has been shown and described with respect to exemplary embodiments thereof, various other changes, omissions and additions in form and detail thereof may be made without departing from the spirit and scope of the invention.

What is claimed is:

1. A prosthetic trial for determining the required dimensions of a prosthetic component, comprising:
   a stem having a proximal end and a distal end, the proximal end including a reduced diameter portion;
   a body including a bore and defining a trunnion, the body being rotatably engaged with the stem, and the bore being dimensioned to receive the reduced diameter portion of the stem; and
   a locking mechanism, insertable within the body, that defines a portion of the bore, wherein the locking mechanism is movable from a first position to a second position to increase the diameter of the bore, and wherein the locking mechanism is effective to inhibit movement of the reduced diameter portion of the stem within the bore of the body.

2. The prosthetic trial of claim 1, wherein the trunnion includes a transverse bore therethrough.

3. The prosthetic trial of claim 1, wherein the stem is curved.

4. A prosthetic trial for determining the required dimensions of a prosthetic component, comprising:
- a stem having a proximal end and a distal end, the proximal end including a reduced diameter portion;
- a body including a bore and defining a trunnion, the body being rotatably engaged with the stem, and the bore being dimensioned to receive the reduced diameter portion of the stem;
- a locking mechanism that defines a portion of the bore, wherein the locking mechanism is movable from a first position to a second position to increase the diameter of the bore, and wherein the locking mechanism is effective to inhibit movement of the reduced diameter portion of the stem within the bore of the body; and
- a second locking mechanism for retaining the locking mechanism in the first position.

5. The prosthetic trial of claim 4, wherein the second locking mechanism includes an element biased against the locking mechanism and engagable with therewith when the locking mechanism is in the first position.

6. A prosthetic trial comprising:
- a body defining a trunnion and a bore;
- a stem having a proximal portion and a distal portion, the proximal portion having a diameter that is less than that of the distal portion, the proximal portion being received within the bore of the body; and
- a locking mechanism movably engaged with the body, wherein the locking mechanism defines a portion of the bore, and wherein moving the locking mechanism from a first position to a second position changes the diameter of the bore, wherein the stem is movable longitudinally and rotationally with respect to the body, and wherein the stem is curved and the rotational orientation of the stem with respect to the body is limited to a first orientation and a second orientation that are 180 degrees apart.

7. The prosthetic trial of claim 6, further comprising complimentary structures that are matable to inhibit rotation of the body with respect to the stem.

8. The prosthetic trial of claim 7, wherein the complimentary structures are mated and unmated by moving the stem longitudinally.

9. The prosthetic trial of claim 8, wherein the complimentary structures include a notch and a tang.

* * * * *